United States Patent [19]
Tiainen et al.

[11] Patent Number: 6,129,944
[45] Date of Patent: Oct. 10, 2000

[54] PRODUCT, A METHOD FOR ITS PRODUCTION, AND ITS USE

[75] Inventors: Ilkka Tiainen, Helsinki; Juha Nurmi, Kirkkonummi; Leena Klasi, Jokioinen, all of Finland

[73] Assignee: Suomen Sokeri Oy, Helsinki, Finland

[21] Appl. No.: 09/269,100

[22] PCT Filed: Sep. 26, 1997

[86] PCT No.: PCT/FI97/00585

§ 371 Date: May 17, 1999

§ 102(e) Date: May 17, 1999

[87] PCT Pub. No.: WO98/13023

PCT Pub. Date: Apr. 2, 1998

[30] Foreign Application Priority Data

Sep. 27, 1996 [FI] Finland .................................. 963904

[51] Int. Cl.[7] .............................. A23D 9/007; A23L 1/06
[52] U.S. Cl. .................. 426/577; 426/601; 426/603; 426/639; 426/658
[58] Field of Search ..................... 426/578, 603, 426/601, 615, 577, 658, 639

[56] References Cited

U.S. PATENT DOCUMENTS

| | | | |
|---|---|---|---|
| 3,881,005 | 4/1975 | Thakkar et al. | 424/238 |
| 4,124,607 | 11/1978 | Beaton | 260/397.25 |
| 4,195,084 | 3/1980 | Ong | 424/238 |
| 5,244,887 | 9/1993 | Straub | 514/182 |

FOREIGN PATENT DOCUMENTS

| | | |
|---|---|---|
| 934686 | 8/1963 | United Kingdom . |
| WO 92/19640 | 11/1992 | WIPO . |

OTHER PUBLICATIONS

The American Heritage Dictionary 3rd edition 1992 Houghton Mifflin Co. Electronicversion.

Whistler 1959 Industrial Gums Academic Press, New York p 565–594.

Method Product Information The Dow Chemical Co. Midland Michigan May 1982.

Potter 1973 Food Science AVI Publishing Co, Inc Westport CT p 632.

*Primary Examiner*—Carolyn Paden
*Attorney, Agent, or Firm*—Scully, Scott, Murphy & Presser

[57] ABSTRACT

The invention relates to a product containing a microcrystalline plant sterol, a method for producing the product by pulverization, and use of the product for the manufacture of edible products. The invention also relates to products manufactured using the microcrystalline plant-sterol-containing product. Preferably, the product is a spread based on a combination of a sweetening agent, a microcrystalline plant sterol and suitable berry or fruit.

47 Claims, 2 Drawing Sheets

PRODUCT, A METHOD FOR ITS PRODUCTION, AND ITS USE

FIELD OF THE INVENTION

The invention relates to a product containing a microcrystalline plant sterol, to a method for producing the product through pulverization, and to the use of the product for producing edible products. The invention also relates to products produced by using this product containing a microcrystalline plant sterol. A preferred product is a spread based on a combination of a sweetening agent, a microcrystalline plant sterol and a suitable berry or fruit.

BACKGROUND

The cholesterol-lowering effect of plant sterols has been known since the 1950's, and the literature of the field therefore includes several reports concerning the positive effects of plant sterols on the cholesterol level. New reports include for example the research by Heinemann et al., Eur. J. Clin. Pharmacol. 40 (Suppl. 1), 1991, 59–63, about the effect of sitostanol and sitosterol on the absorption of cholesterol in the intestine by using the intestinal perfusion technique. Sitostanol was found to reduce the cholesterol absorption by as much as 85% and the sitosterol absorption by 50%.

Nevertheless, the use of plant sterols has not been very extensive, due to for example their poor availability and therefore high price. One of the greatest problems has been the poor solubility of plant sterols, since they are not soluble in water and are also poorly soluble in fats. There have been efforts to solve the solubility problem by forming fat-soluble forms of plant sterols, for example fatty acid esters, and by using them in connection with fats.

GB 934,686 (Boehringer & Söhne) discloses a therapeutic preparation containing sitosterol, 1–4% by weight of gelatine or 0.1–2% by weight of methyl cellulose and a crystalline sugar as a filler. For preparation, sitosterol and sugar are ground and then combined in a blend of gelatine or methyl cellulose in water. According to said document the suspension obtained is no longer thixotrophic, which is very surprising, because gelatine and methyl cellulose are generally regarded as thickening agents. It is also mentioned that e.g. alginates or other cellulose derivatives do not have a corresponding effect. The invention described in GB 934,686 is, hence, based on the specific effect of either of two specific compounds, gelatine or methyl cellulose, in the sitosterol suspension.

An example of a method for preparing a fatty acid ester is the method disclosed in EP 195,311 (Yoshikawa Oil & Fat Co., Ltd.) wherein a plant sterol and a branched aliphatic primary or secondary alcohol having 14 to 32 carbon atoms is reacted with a fatty acid or fatty acid ester in the presence of lipase or cholesterol esterase in an aqueous solution or in a water-containing organic solvent. DE 2,035,069 (Procter & Gamble Co.) discloses the preparation of carboxylic acid esters of plant sterols with an acylation reaction by using perchloric acid as a catalyst. The obtained plant sterol ester is then added to a cooking or salad oil to produce an oil that reduces the cholesterol level.

WO 92/19640 (Raision Margariini Oy) discloses a β-sitostanol fatty acid ester that is prepared by esterifying a β-sitostanol mixture with a fatty acid ester or ester mixture in the presence of an interesterification catalyst. The obtained fatty acid ester is suggested to be used as a part of fats or oils in fat-containing products; a preferred embodiment is the addition of the ester to edible fats. The reference also discloses by way of comparison the effect of β-sitostanol that has been emulsified into rape-seed oil on serum cholesterol levels. The result is not statistically significant and it is considered marginal as compared with the effect of the β-sitostanol ester described in the reference.

EP 289,636 (Asahi Denka Kogyo Kabushiki Kaisha) relates to an emulsified or solubilized sterol composition wherein the sterols are emulsified or solubilized in an aqueous solution of polyhydroxy compounds containing sucrose and/or polyglycerol fatty acid esters or in liquid polyhydroxy compounds containing these fatty acid esters. The reference discloses that no solvent, such as fat or oil, is used for dissolving the sterols. However, the composition contains as an essential ingredient sucrose and/or polyglycerol fatty acid esters that are used in an amount of 0.5 to 10 parts by weight per part by weight of the sterol. The product is stated to be stable and useful for example in foodstuffs, cosmetics, drugs and agricultural chemicals. These final products are not described in greater detail.

U.S. Pat. No. 5,244,887 (Straub) discloses food additives containing plant stanols. The stands include sitostanol, clionastanol, 22,23-dihydrobrassicastanol, campestanol, and mixtures thereof. In order to prepare the food additive, a solution, suspension or emulsion of stanols is prepared by mixing the stanol with a solubilizing agent, an antioxidant and a dispersing agent. A preferred product is a composition containing about 74.8% vegetable oil, about 1.2% tocopherol and about 25% stanols. The additive is added to foodstuffs containing cholesterol, for example to meat, eggs and dairy products, and the purpose is to prevent the absorption of cholesterol from these foodstuffs.

The background art thus describes efforts to improve the solubility and therefore the range of use of plant sterols by forming fat-soluble derivatives from the sterols; the plant sterols and the aforementioned derivatives are dissolved or emulsified in a fat or a fat component and they are used as additives in fat-containing foodstuffs to prevent the absorption of cholesterol from these foodstuffs.

SUMMARY OF THE INVENTION

The object of the present invention was to provide such a form of a plant sterol that is useful as such and that can be produced in a simple and economic manner without harmful additives.

According to the present invention, these aims are achieved by using a microcrystalline plant sterol instead of a crystalline plant sterol.

DESCRIPTION OF THE PREFERRED EMBODIMENTS

The invention therefore relates to a product containing a crystalline plant sterol, the product being characterized in that the plant sterol is in a microcrystalline form.

The volumetric mean particle size of the product according to the invention containing a microcrystalline plant sterol is less than 35 μm, preferably less than 30 μm and more preferably less than 25 μm, for example 20 to 23 μm. The volumetric mean particle size is most preferably a great deal lower than these values, for example about 4 to 15 μm, in particular 5 to 10 μm. When the volumetric mean particle size is about 10 to 20 μm, preferably at most 15% of the particles have a size exceeding 30 μm.

Figure 1:
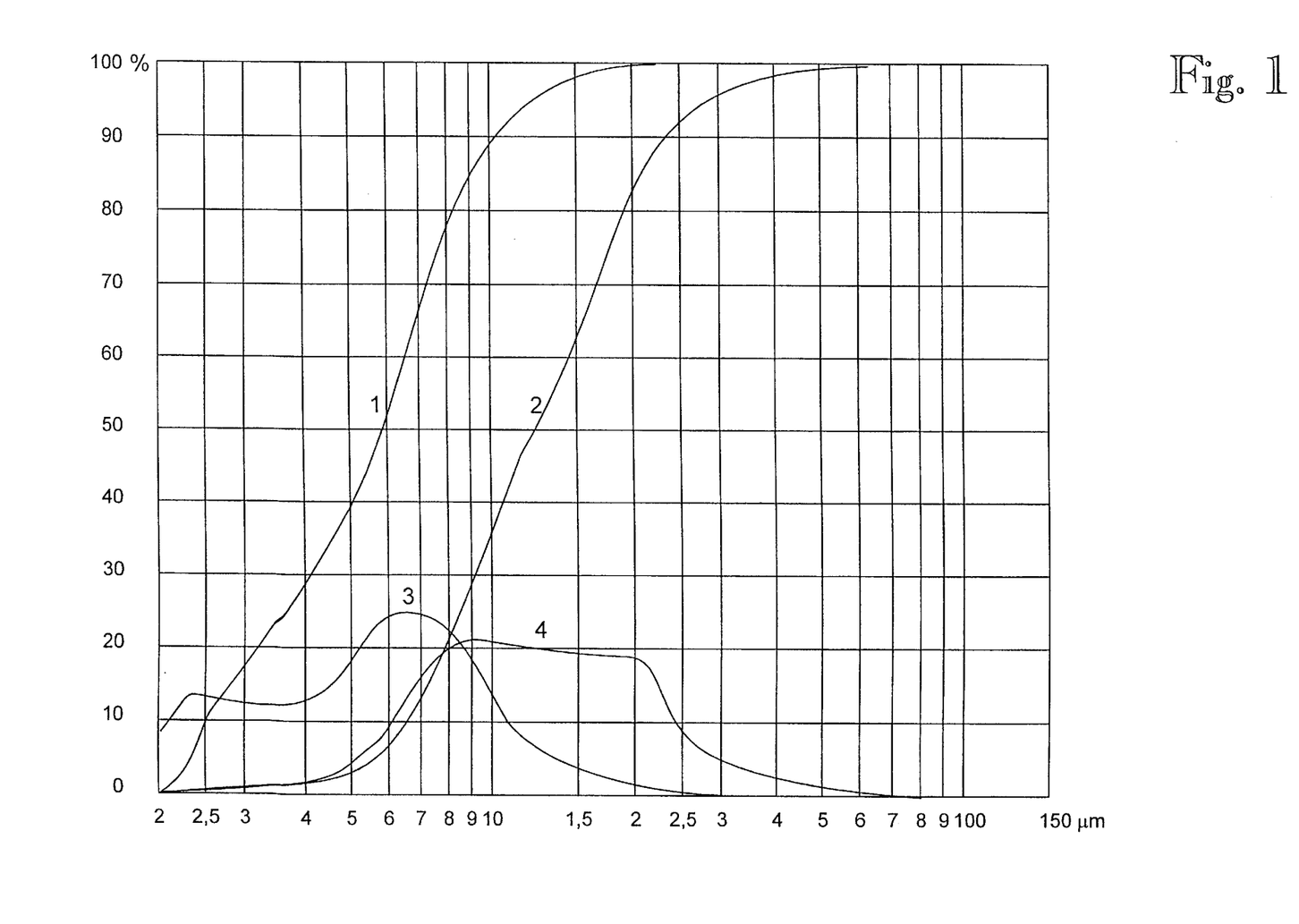
FIG. 1 shows the particle size and volume distributions of a plant sterol pulverized into microcrystalline form according to the invention for examples 1 to 4.
Figure 2:
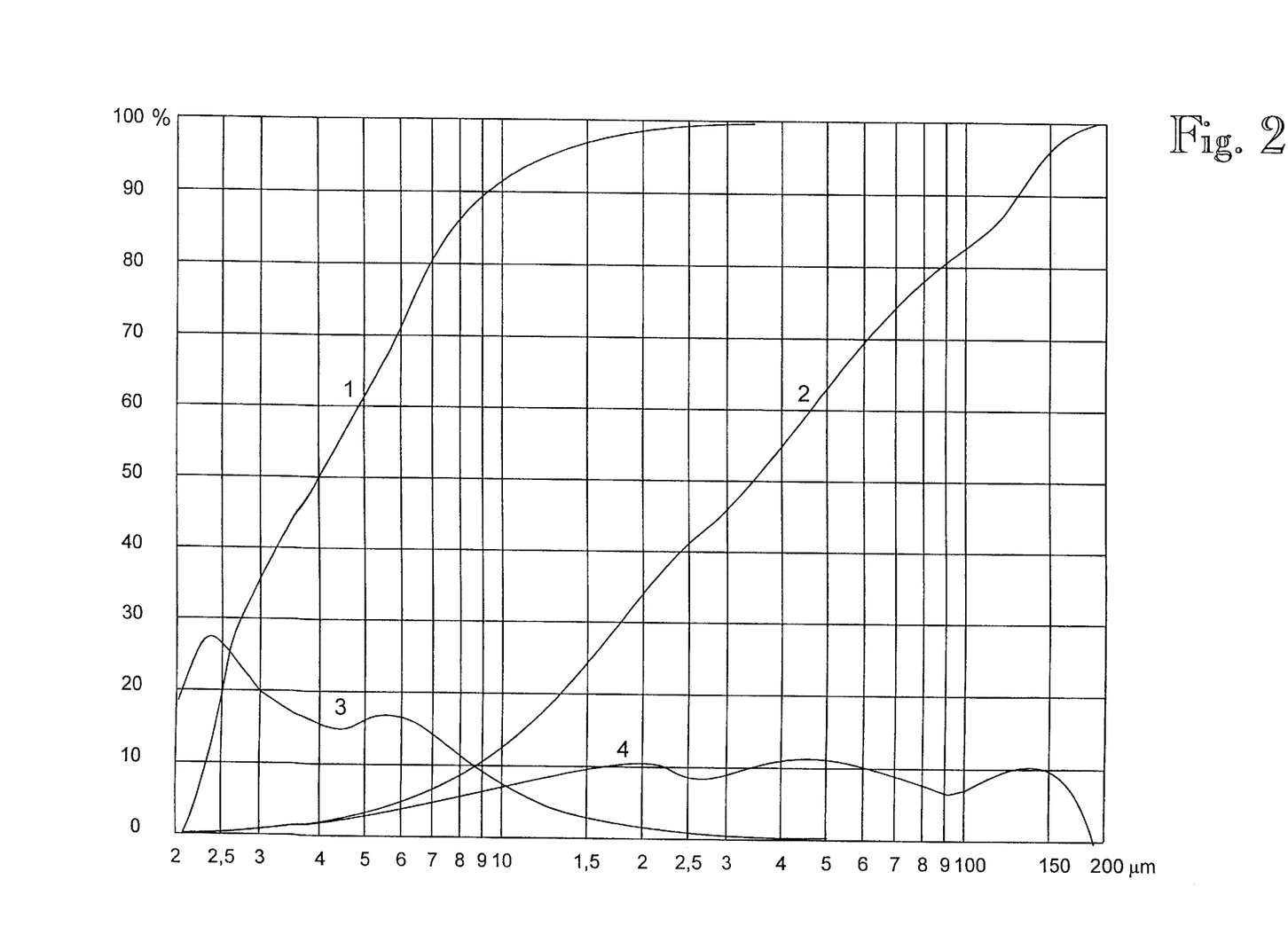
FIG. 2 shows the particle size and volume distributions of a crystalline plant sterol that has not been pulverized for examples 1 to 4.

The particle size and volume distributions of a plant sterol pulverized into a microcrystalline form according to the invention and a crystalline plant sterol that has not been pulverized and that is used as reference material are shown in FIGS. 1 and 2, respectively. The assays were carried out by the PAMAS method in an aqueous solution to which a small amount of tenside had been added. The difference between the microcrystalline plant sterol according to the invention (Example 3) and the untreated crystalline plant sterol is very clear. The size and volume distributions of the non-pulverized sample are very broad, including both very small particles and a great number of large particles that prevent the addition of a crystalline plant sterol as such to edible products, causing both technical problems and problems with taste and structure. The microcrystalline plant sterol according to the invention is in turn clearly more homogenous and contains substantially fewer large particles.

A plant sterol here refers to a phytosterol that reduces the cholesterol level. The plant sterol is preferably β-sitosterol, i.e. 24-ethyl-5-cholesten-3β-ol, or especially its hardened form β-sitostanol, i.e. 24-ethyl-5α-cholesten-3β-ol. Other suitable plant sterols include for example campestenol and clionastanol. Commercially available plant sterols are often mixtures of plant sterols that are also appropriate for use according to the present invention.

A microcrystalline plant sterol can be formed by pulverization according to the present invention.

The invention therefore also relates to a method for preparing a product containing a crystalline plant sterol, the method being characterized in that the crystalline plant sterol is pulverized into a microcrystalline form.

The pulverization can be carried out both as dry grinding and wet grinding. The dry grinding can be performed for example with a counterjet pulverizer wherein the particles that have been fluidized into a carrier gas, typically air, and that are to be pulverized are conducted to collide at a high speed. The pulverizer preferably comprises a classifier where the pulverized material is classified into fractions having different particle sizes. Other grinding apparatuses based on kinetic energy can also be used for carrying out the dry grinding. The dry grinding can also be carried out in mills based on the use of friction, for example in a ball mill. The wet grinding is performed preferably in mills of the aforementioned type based on the use of friction. The parameters used in the grinding are determined according to the structure of the grinding device used and the substance or mixture to be pulverized.

The pulverization can be carried out on a crystalline plant sterol as such or on a mixture of a plant sterol and another component, such as a suitable admixture. According to the present invention, the pulverization is carried out preferably on a mixture of a plant sterol and a sweetening agent.

The sweetening agent can be for example a normal sugar, such as sucrose, glucose or fructose, an aqueous solution of sugar, a starch syrup, isoglucose, isomalt, a sugar alcohol, such as sorbitol, lactitol or xylitol. The sugar can also be replaced with a mixture of a builder and a sweetening agent. The builder can be polydextrose or inulin and the sweetening agent can be an intense sweetener, a carbohydrate sweetener or a mixture thereof. The amount of the sweetening agent can vary depending on the method used and the desired final product. In sweet spreads, a sweetening agent and a plant sterol are usually used in the ratio of about 0.5:9.5 to 9.5:0.5, preferably about 3:7 to 9:1, most preferably about 4:6 to 6:4 and particularly about 1:1. The spreads do not always contain a sweetening agent. The function of sugar as a builder can be replaced in both sweet and other spreads with other builders. According to the present invention, a microcrystalline plant sterol can also be included in fat-containing spreads, such as margarine, cheese spread, pastes etc., having a low sugar content or containing no sugar.

According to the present invention, a separate homogenization stage can be carried out in addition to pulverization. The homogenization stage can be carried out both before and after the pulverization. According to the present invention, also the homogenization stage is carried out preferably on a mixture of a plant sterol and another component.

In a preferred embodiment of the present invention, a non-homogenous mixture or suspension of a plant sterol and a liquid phase, such as water or an aqueous solution, is formed first. This is converted into a homogenous presuspension by mixing for example with a blender preferably at a high mixing speed and/or by using a great shear force. It is preferable for the homogeneity of the presuspension that the dry substance content and viscosity of the liquid phase are rather high. Thus it is preferable to prepare the premixture in a sugar-containing syrup instead of pure water. Most preferably, a liquid sugar or a sugar syrup having a dry substance content of at least 65% is used. The proportion of the plant sterol is preferably 10% or more, particularly as much as 50% based on the dry substance content. It has been found out in connection with this invention that when a syrup containing a plant sterol and sugar is mixed effectively, after a treatment of 20 minutes in a domestic blender the plant sterol crystals were completely wet and no crystal agglomerates were formed even after a long storage period.

The suspension is subjected thereafter to a pulverization treatment wherein the plant sterol crystals in the suspension are pulverized into microcrystals. For example ball mills are suitable for this purpose, as stated above.

In a second preferred embodiment of the present invention, especially in large-scale production, pulverization is carried out first, preferably on a mixture of a plant sterol and an admixture, such as a sweetening agent. The pulverized mixture can also be homogenized or suspended.

According to the present invention, a mainly mechanical treatment is carried out; no esterification is performed and no other derivatives are produced either, and no solvents or other non-edible admixtures are required. The method according to the invention is much simpler than chemical methods, and the product will not contain any harmful residues of solvents, catalysts or admixtures. It should also be noted that the derivatives that are made highly soluble according to prior art methods can release a very poorly soluble sterol to the organism when they decompose and possibly cause risks of precipitation. Such significant changes in solubility do not occur when a microcrystalline plant sterol is used according to the present invention.

The product according to the invention containing a microcrystalline plant sterol has a cholesterol-lowering effect. The product can be used as such. It can also be used as an ingredient in cholesterol-lowering products, such as functional foodstuffs, natural products and pharmaceuticals. A microcrystalline plant sterol homogenized into a fat or an aqueous solution is applicable for use especially in the manufacture of other edible cholesterol-lowering products; the degree of processing of the sterol is suitable for the industry and no processing problems occur during its use.

When a microcrystalline plant sterol was added according to the present invention to edible products, the plant sterol had no harmful effects on the structure, taste or mouth-feel of the final product. Unpleasant taste or aftersensations reported earlier in connection with plant sterols were not found.

The invention thus relates further to the use of a product containing a microcrystalline plant sterol as a cholesterol-lowering agent and to its use for the manufacture of edible products.

The present invention also provides edible cholesterol-lowering products, which contain a microcrystalline plant sterol according to the invention in addition to the other conventional ingredients.

A spread based on a combination of a sweetening agent, a microcrystalline plant sterol and a suitable berry or fruit is disclosed in the invention as a preferred edible cholesterol-lowering product. It has been proved in connection with the present invention that it is possible to use in the product a microcrystalline plant sterol as such without any technological problems. There are no problems in the product that can be detected by sensory evaluation and that relate to taste or structure. The product can be used in the same manner as fats or marmalade for example on bread or other bakery products. The product can replace the use of butter or margarine and it has several advantageous characteristics over them.

Due to the plant sterol, the product has a cholesterol-lowering effect. The use of the product also directly reduces the total intake of fat since no fat, but a non-fat spread, is put on bread. At the same time, especially the use of hardened fats can be reduced. Thus the proportion of fats and salt of the total intake of energy decreases, which is recommendable for serum cholesterol level and blood pressure. The product makes the diet lighter, since the spread contains less than half of the energy content of butter or margarine and about 25 to 30% less energy than light fats having a fat content of 40%. The use of the product also decreases the intake of salt, since it does not require the addition of any salt, whereas fats usually contain about 0.5 to 1.5% of salt. Decreasing the intake of salt and especially sodium is highly recommendable for health, as is well known. Compared with fats, the product also has a clearly longer shelf life.

The sweetening component of the preferred spread according to the invention can be a conventional sugar, such as sucrose for example in the form of normal granulated sugar, glucose or fructose, or special sugars, such as preservation sugar, containing for example a jellying agent and/or a preservative. If desired, the sweetening component can be an aqueous solution of sugar or several sugars, a mixture of several sugars, or it can partly consist of products that are obtained during the refinement of sugar or that are manufactured specifically, such as liquid sugars, sugar syrups or mixtures thereof. The sweetening component of the product or a part of it can also be, if desired, for example starch syrup, isoglucose, polyol, such as sorbitol or xylitol, polydextrose or an intense sweetener in addition to the other usual sweetening agents.

Suitable berries for the preferred spread according to the present invention include, for example, strawberry, blueberry, boysenberry, lingonberry, gooseberry, raspberry, blackberry and currants. Examples of suitable fruits include, for example, orange and other citrus fruits, apricot, apple, peach, plum and cherry. It is evident that the spread according to the invention can also contain different combinations of berries and/or fruits.

The plant sterol can be selected, as stated above, from several different plant sterols or plant sterol mixtures. Preferable sterols are β-sitosterol and especially β-sitostanol.

The product can be supplemented, if desired, with usual additives and other additional agents, such as jelling and thickening agents, preservatives, acidity-regulating agents, flavourings, aromatic agents etc.

The spread according to the present invention can therefore have for example the following composition:

| Fruit and/or berry | 20–60% |
|---|---|
| Sweetening agent | 20–60% |
| Plant sterol | 0.5–10% |
| Jellying agent | 0–5% |
| Preservatives | 0–0.1% |
| Water | ad 100% |

The product preferably comprises about 30 to 50%, preferably 40 to 48% of fruit and/or berry, and about 30 to 55%, most preferably about 40 to 50% of a sweetening agent. Pectin can preferably be used as the jellying agent. The preservatives can be usual preservatives, such as potassium sorbate. The product can also be supplemented, if desired, with other usual additives, such as citric acid, as an acidity-regulating agent. By changing the ingredients of the product and the method of manufacture the spread can be prepared for example in the form of jam, marmalade or jelly. In a corresponding manner, with the microcrystalline plant sterol according to the present invention it is also possible to produce beverages, such as nectars.

The cholesterol-lowering effect of a plant sterol can be increased by using pectin in the products of the invention that contain a microcrystalline plant sterol, usually in an amount of about 0.1 to 2%, preferably 0.2 to 1%, most preferably 0.4 to 0.6%. In addition to intensifying the effect of the plant sterol, pectin also has a positive effect on the product structure. It is also noted that the berries and/or fruits contained in the preferred spread according to the invention also inherently contain pectins.

A product corresponding to the spread according to the invention, based on a combination of a sweetening agent, a plant sterol and a suitable berry or fruit, can also be prepared by replacing the berries or fruits with molasses, such as a sugar syrup containing trace elements, or a mixture of sugar syrup and starch syrup. The product can be supplemented with a thickening agent, if desired. The structure of the product according to the invention that contains a microcrystalline plant sterol and that is based on molasses corresponds to honey or peanut butter and it has all the advantages of the above-described spread based on berries or fruits.

It is also possible to use sugar and different sweetening products, such as special sugars containing small amounts of a jellying agent and/or a preservative and intended for jam-making or for baking, to manufacture, according to the present invention, corresponding functional cholesterol-lowering sweetening products by adding a microcrystalline plant sterol thereto. The edible cholesterol-lowering products according to the invention also include different sugar-containing products and spice-sugar mixtures to which a microcrystalline plant sterol has been added according to the present invention.

Examples of other functional products according to the invention that contain a sweetening agent and a microcrystalline plant sterol include different sweets, such as marmalades, chocolate, sugar candies and chewing gums; nectars and other beverages; different desserts based on milk or fruit, such as puddings and creams; yoghurts, salad dressings, such as mayonnaise, etc.

The sugar content of the functional products according to the invention that contain a sweetening agent can be about 1 to 99%, in preferred products about 45 to 95%. The functional sweetener products according to the invention contain about 0.5 to 15%, preferably about 1 to 10% of a plant sterol. It should be understood, however, that these values, as all the other numerical values given in this specification, are only trend-setting values. According to the invention, it is therefore possible to use all amounts sufficient for achieving the desired effect and having no negative effect on the structure or taste of the final product.

The microcrystalline plant sterol according to the invention can also be prepared and used without an added sweetening agent. Therefore also all the other edible cholesterol-lowering products containing a microcrystalline plant sterol fall within the scope of the present invention. They include especially products that are based on fats and that contain a microcrystalline plant sterol, for example vegetable oil and/or fats or animal fats containing a microcrystalline plant sterol, or mixtures thereof. The microcrystalline plant sterol mixes well with fat-containing foodstuffs, such as soft margarine and baking margarine or mayonnaise, both as such and as a mixture of a plant sterol and a sweetening agent. It is easy to prepare a homogenous mixture also at room temperature. A microcrystalline plant sterol can also be added to bakery products and/or to products used in their preparation both as such and as a mixture with for example a sweetening agent, fat, flour or some other suitable component.

One of the most important advantages of edible cholesterol-lowering products according to the invention is that the plant sterol is brought to the consumers in such a form that is easy to use.

The edible cholesterol-lowering products according to the invention are prepared in the same manner as the corresponding conventional products by adding a desired amount of a microcrystalline plant sterol, which has optionally been homogenized, at a suitable stage of the preparation.

The microcrystalline plant sterol according to the invention is also applicable for use in pharmaceutical products, as already stated. These products are also prepared by methods that are common in the field, adding a desired amount of a microcrystalline plant sterol, which has optionally been homogenized, at a suitable stage of the preparation.

The invention will be described in greater detail by means of the examples below. The examples are only provided to illustrate the invention and they should not be considered to restrict the scope of the invention.

EXAMPLE 1

Preparation of a homogenized microcrystalline plant sterol 150 g of sitostanol (Kaukas Oy) was added as such to 2310 g of Neste 65 syrup (Porkkalan Sokeripuhdistamo Oy). The mixture was homogenized with a blender (Braun, type 4259) for 30 min, whereafter the suspension was pulverized for 17 h in a large porcelain ball mill.

EXAMPLE 2

Preparation of a homogenized microcrystalline plant sterol 50 g of sitostanol was added as such to 650 g of Neste 77 syrup (Porkkalan Sokeripuhdistamo Oy). The mixture was homogenized and a presuspension was formed with a blender (Braun, type 4259) for 30 min, whereafter the suspension was pulverized for 17 h in a large porcelain ball mill.

EXAMPLE 3

Preparation of a microcrystalline plant sterol 20 kg of sitosterol (Kaukas Oy) was added as such to 180 kg of sucrose and the mixture was jet-pulverized with a dry tumbling grinder using a classifier (Oy Finnpulva Ab, grinder FP3P, classifier FPC15R). The carrier gas was air having a temperature of 63° C. and a feed pressure of 2.4 bar.

EXAMPLE 4

Preparation of a microcrystalline plant sterol 4530 g of sitostanol was jet-pulverized as such with a dry tumbling grinder using a classifier (Micropulva). Air was used as the carrier gas. The about 500 g coarse fraction obtained at the first stage was resupplied to the grinder and was vibrated, whereby a very particulate product was obtained.

EXAMPLE 5

Preparation of a microcrystalline plant sterol

Example 4 was repeated using 4100 g of sitostanol. At the first stage, 1250 g course fraction was obtained and subsequently re-supplied to pulverization, simultaneously increasing the feed rate and flushing air.

EXAMPLE 6

Preparation of a homogenized microcrystalline plant sterol 2000 g of microcrystalline powder prepared according to example 3 and containing 200 g of sitosterol and 1800 g of sugar was mixed with 1077 g of water and 200 g of sugar, and a homogenous suspension was formed of the substances by blending for 30 min with a blender (Braun, type 4259).

EXAMPLE 7

Preparation of a homogenized microcrystalline plant sterol 2000 g of microcrystalline sitosterol-sugar powder prepared according to example 3 was mixed with 260 g of Neste 77 sugar liquid to which 538 g of water had been added (Porkkalan Sokeripuhdistamo Oy), and a homogenous suspension was formed of the substances with a blender in the above-described manner.

EXAMPLE 8

Berry-based spread

A product of the type of a breakfast marmalade to be spread was prepared according to the following basic recipe:

|  | g |
| --- | --- |
| Water | 200 |
| Strawberry | 500 |
| Sweetening agent | 500 |
| Pectin | 6.1 (+30 g of sugar or water) |
| Potassium sorbate (20%) | 6.5 |
| Citric acid (50%) | 7.8 |

The strawberries were mashed, the mashed strawberries and water were mixed, and the mixture was cooked for a few minutes. Pectin (LM) mixed in a small amount of sugar and/or hot water was added to the mixture, which was heated for a few minutes. 820 g of a sitostanol-liquid-sugar mixture prepared according to example 1 was then added and the cooking was continued for a few minutes. An acidity-regulating agent and a preservative (one or both of them can be left out, if desired) were added to the mixture. The mixture was cooked further until the weight was 1150 g, whereafter the product was allowed to cool to 60° C. and packed for example in jars or in containers holding one serving.

In sensory evaluation, the spread was found to have an excellent structure and taste. However, some of the panel members found the mouth-feel to be a bit sandy.

EXAMPLE 9

Berry-based spread

A product of the type of a breakfast marmalade to be spread was prepared on the basis of example 8 by using strawberry but with 700 g of a sitosterol-liquid-sugar mixture prepared according to example 7. When the marmalade was prepared, less water had to be evaporated than in the product described in example 8, wherefore also the time of cooking was shorter.

In sensory evaluation, the taste and structure of the spread were found to correspond to the product described in example 6.

EXAMPLE 10

Berry-based spread

A product of the type of a breakfast marmalade to be spread was prepared on the basis of example 9 using strawberry but increasing the dry substance content. The target weight was 900 g, the calculated dry substance content was about 63 Bx, the actual dry substance content was 70 Bx (the plant sterol increases the Bx value). No preservative was added.

In sensory evaluation, the spread was found to have a different taste than the previous product. The spread did not have a sandy mouth-feel, but both the structure and the taste were considered excellent.

EXAMPLES 11 AND 12

Berry-based spread

A product of the type of a breakfast marmalade to be spread was prepared in the manner described in example 8, but strawberries were replaced with a corresponding amount of raspberries or boysenberries, and a sitostanol-liquid-sugar mixture prepared according to example 2 was used.

The products were marmalades with a beautiful colour and in sensory evaluation they were found to have an excellent colour, taste, mouth-feel and structure. There was nothing powdery or sandy in these products.

EXAMPLE 13

Fruit-based spread

A product of the type of a breakfast marmalade to be spread was prepared according to the basic recipe described in example 8, but strawberries were replaced with a corresponding amount of orange pureed with a food press, and a sitostanol-liquid-sugar mixture prepared according to example 2 was used.

The pureed oranges and water were mixed and the mixture was cooked for a few mixtures. Pectin mixed in a small amount of sugar was added to the mixture and the mixture was heated for a few minutes. The stanol-sugar mixture was added and cooking was continued until the dry substance content was about 51% and the weight was about 1000 g. A preservative and an acidity-regulating agent were added to the mixture, it was allowed to cool to 80 to 85° C. and packed for example in jars or in containers holding one serving. The preservative and the acidity-regulating agent can be left out, if desired.

In sensory evaluation the product was found to have an excellent colour, taste, mouth-feel and structure. There was nothing powdery or sandy in the product.

EXAMPLES 14 TO 17

Fruit-based spread

A product of the type of a breakfast marmalade to be spread was prepared in the same manner as in example 13, but the oranges were replaced with a corresponding amount of apple, plum, peach or apricot pureed with a food press. The plums and the apricots were dried products that were soaked in water overnight. When apple marmalade was prepared, the amount of pectin was reduced to a half.

When the amount of pectin is changed, it is possible to prepare products with varying stiffnesses; due to the small amount of pectin the apple spread was therefore less thick than the other spreads. The apple spread also had a slightly pale colour; this can be avoided by selecting an apple variety with a strong colour or by adding a small amount of a colouring.

Some of the panel members found the plum spread to be too solid, which can be avoided by decreasing the dry substance content of the product and/or by reducing the amount of pectin.

In sensory evaluation the products were found to have an otherwise excellent taste, mouth-feel and structure. There was nothing powdery or sandy in the products. The apricot and peach spreads were considered especially successful.

EXAMPLE 18

Berry-based spread

A product of the type of a breakfast marmalade to be spread was prepared of strawberry in the manner described in example 8, but with the mixture of a microcrystalline plant sterol and a sweetening agent prepared according to example 3. The mixture was added as such, without forming a suspension, directly to the marmalade concoction. The mixture blended well with the concoction and no technical problems occurred.

In sensory evaluation the product was found to have an excellent colour, taste, mouth-feel and structure. There was nothing powdery or sandy in the product.

EXAMPLE 19

Syrup

A plant-sterol-sugar mixture prepared according to example 3 was added as such to baking syrup and mixed. The pulverized mixture blended effectively with the syrup that was at room temperature and had a high dry substance content and viscosity, and the structure of the final product was very smooth. A suitable thickening agent, such as xanthan, can be added to the product, if desired, to regulate the structure to be suitable for a spread.

EXAMPLE 20

Fat-containing emulsion

To form an emulsion, a sucrose-sitosterol mixture 90:10, ground according to example 3, was dissolved in rape-seed oil (Menu, Raisio Oy). An extra fine icing sugar correspondingly dissolved in rape-seed oil was used as a control.

The amounts of dry substance shown in Table 1 were measured into a blender. The mixture was mixed at full speed for 30 min with the blender. A homogenous emulsion was formed. The emulsions were poured into a glass container and allowed to rest at room temperature.

TABLE 1

Mixtures and their weighings

| Experiment | Dry substance, g | Cooking oil, g |
|---|---|---|
| 1 sucrose-sitosterol (90:10): oil 25:75 | 73.19 | 219.48 |
| 2 sucrose-sitosterol (90:10): oil 50:50 | 188.96 | 188.62 |
| 3 icing sugar: oil 25:75 | 95.35 | 285.84 |
| 4 icing sugar: oil 50:50 | 216.70 | 216.83 |

Immediately after a mixing in the blender the mixtures were homogenous and milky, excluding the mixture of icing sugar and oil in the ratio of 50:50, which was a very thick mayonnaise-like homogenous mixture. The thicknesses of the mixtures depended on the proportions of oil and dry substance. Table 2 shows sensory evaluation at different times after the mixing.

TABLE 2

Sensory evaluation of sucrose-sitosterol-oil mixtures

| Experiment | Time | | | |
|---|---|---|---|---|
| | 3 h | 1 day | 2 days | 5 days |
| 1 sucrose 90%: oil 25:75 | homogenous, milky | homogenous, milky | separate layer of oil | separate layer of oil |
| 2 sucrose 90%: oil 50:50 | homogenous, milky | homogenous, milky | homogenous, milky | homogenous, milky |
| 3 icing sugar: oil 25:75 | homogenous, milky | separate layer of oil | separate layer of oil | separate layer of oil |
| 4 icing sugar: oil 50:50 | thick "mayonnaise" | thick "mayonnaise" | thick "mayonnaise" | thick "mayonnaise" |

EXAMPLE 21

Liquid margarine 100 g of jet-pulverized (Finnpulva) sugar-plant-sterol mixture was added to 200 g of liquid margarine (Sunnuntai®, Raisio Oy) and mixed. The mixture of sugar and plant sterol mixed well with the liquid margarine. The microcrystalline plant sterol does not form great lumps, but there is a slight mouth-feel and some small lumps. 200 g of the aforementioned liquid margarine of Raisio was added; when the dry substance content decreased, the mouth-feel became considerably smoother.

EXAMPLE 22

Soft margarine

5% of sitostanol and sitostanol-sterol preparations ground in pure form by a jet-pulverizing method according to examples 4 and 5 were mixed with a soft margarine (Keiju, Raisio). The products mixed well, forming a smooth spread, from which the powder added cannot be distinguished by the naked eye. When the spread was used, no particles were detected in the product in sensory evaluation when the product was tasted as such.

EXAMPLE 23

Fat-containing emulsion

5% of plant sterol preparations ground according to examples 4 and 5 were mixed with rape-seed oil (Kultasula, Raisio). Mixing yielded a homogenous emulsion.

What is claimed is:

1. A product containing a plant sterol, characterized by consisting essentially of a microcrystalline plant sterol, a sweetening agent and water.

2. The product according to claim 1 wherein the volumetric mean particle size of the microcrystalline plant sterol is less than 35 μm.

3. The product according to claim 2 wherein the proportion of particles having a volumetric mean particle size exceeding 60 μm is substantially less than 10% in the microcrystalline plant sterol.

4. The product according to claim 2 wherein the volumetric mean particle size of the microcrystalline plant sterol is less than 30 μm.

5. The product according to claim 4 wherein the volumetric mean particle size of the microcrystalline plant sterol is less than 25 μm.

6. The product according to claim 1 wherein the plant sterol is selected from the group consisting of β-sitosterol, β-sitostanol, campestenol, clionastanol and a mixture thereof.

7. The product according to claim 6 wherein the plant sterol is β-sitosterol or β-sitostanol.

8. The product according to claim 7 wherein the plant sterol is β-sitostanol.

9. The product according to claim 1 wherein the sweetening agent is selected from the group consisting of a sugar, an aqueous solution of a sugar, a starch syrup, a sugar alcohol, polydextrose and an intense sweetener.

10. The product according to claim 6 wherein the sweetening agent is an aqueous solution of a sugar or a sugar syrup with a dry substance content of at least about 65%.

11. The product according to claim 1 which is produced by pulverization and homogenization.

12. The product according to claim 1 which is produced using a great shear force.

13. A method for producing a product containing a plant sterol comprising forming a homogenous suspension consisting essentially of a microcrystalline plant sterol and a sweetening agent in an aqueous solution.

14. The method according to claim 13 wherein the crystalline plant sterol and the sweetening agent are subjected, in either order, to pulverization and homogenization.

15. The method according to claim 14 wherein the pulverization is carried out as dry grinding or wet grinding.

16. The method according to claim 15 wherein the pulverization is carried out as dry grinding.

17. The method according to claim 16 wherein the pulverization is carried out as dry grinding before the homogenization.

18. The method according to claim 15 wherein the pulverization is carried out as wet grinding.

19. The method according to claim 18 wherein the pulverization is carried out as wet grinding after the homogenization.

20. The method according to claim 14 wherein the plant sterol is ground to a volumetric mean particle size of less than 35 µm.

21. The method according to claim 14 wherein the plant sterol is ground to a volumetric mean particle size of less than 30 µm.

22. The method according to claim 21 wherein the plant sterol is ground to a volumetric mean particle size of less than 25 µm.

23. The method according to claim 22 wherein the plant sterol is ground to a volumetric mean particle size of less than 20 µm.

24. The method according to claim 14 wherein the homogenization is carried out by mixing with a blender.

25. The method according to claim 24 wherein the homogenization is carried out by using a great shear force.

26. The method according to claim 13 wherein the plant sterol is selected from the group consisting of β-sitosterol, β-sitostanol, campestenol, clionastanol and a mixture thereof.

27. The method according to claim 13 wherein the sweetening agent is selected from the group consisting of a sugar, an aqueous solution of a sugar, a starch syrup, a sugar alcohol, polydextrose and an intense sweetener.

28. The method according to claim 27 wherein the sweetening agent is an aqueous solution of a sugar or a sugar syrup with a dry substance content of at least about 65%.

29. A plant sterol-containing product, characterized by consisting essentially of a microcrystalline plant sterol and fat.

30. The product according to claim 29 wherein the volumetric mean particle size of the microcrystalline plant sterol is less than 35 µm.

31. The product according to claim 30 wherein the volumetric mean particle size of the microcrystalline plant sterol is less than 30 µm.

32. The product according to claim 31 wherein the volumetric mean particle size of the microcrystalline plant sterol is less than 25 µm.

33. The product according to claim 29 wherein the proportion of particles having a volumetric mean particle size exceeding 60 µm is substantially less than 10% in the microcrystalline plant sterol.

34. The product according to claim 29 wherein the plant sterol is selected from the group consisting of β-sitosterol, β-sitostanol, campestenol, clionastanol and a mixture thereof.

35. The product according to claim 34 wherein the plant sterol is β-sitosterol or β-sitostanol.

36. The product according to claim 35 wherein the plant sterol is β-sitostanol.

37. The product according to claim 29 further characterized in that it also contains a sweetening agent.

38. The product according to claim 37 wherein the sweetening agent selected from the group consisting of a sugar, an aqueous solution of a sugar, a starch syrup, a sugar alcohol, polydextrose and an intense sweetener.

39. The product according to claim 37 wherein the sweetening agent is an aqueous solution of a sugar or sugar syrup with a dry substance content of at least about 65%.

40. The product according to claim 29 produced by pulverization and homogenization.

41. An edible product, characterized in that it contains a product according to claim 1 or 29.

42. A method for lowering the cholesterol level in a subject which comprises administering thereto a cholesterol reducing effective amount of a product according to claim 1 or 31.

43. A method for the preparation of an edible food product which comprises adding to a food a cholesterol lowering effective amount of the product according to claim 1 or 31.

44. The method according to claim 43 wherein the food is a spread, fat, confectionary, beverage, yogurt, salad dressing or bakery product.

45. The method according to claim 43 wherein the food is chocolate, nectar, pudding, cream or fat.

46. A spread characterized in that it contains a microcrystalline plant sterol, a sweetening agent and berry and/or fruit.

47. The spread according to claim 46 wherein it also contains pectin.

* * * * *

UNITED STATES PATENT AND TRADEMARK OFFICE
CERTIFICATE OF CORRECTION

PATENT NO.     : 6,129,944                                    Page 1 of 1
DATED          : October 10, 2000
INVENTOR(S)    : Ilkka Tiainen et al.

It is certified that error appears in the above-identified patent and that said Letters Patent is hereby corrected as shown below:

<u>Column 2,</u>
Line 48, insert -- BREIF DESCRIPTION OF THE DRAWINGS --

Signed and Sealed this

Seventh Day of May, 2002

Attest:

JAMES E. ROGAN
Attesting Officer    Director of the United States Patent and Trademark Office